(12) United States Patent
Mombrinie et al.

(10) Patent No.: US 7,666,171 B2
(45) Date of Patent: Feb. 23, 2010

(54) PORTABLE INSTILLATION APPARATUS AND METHOD

(75) Inventors: Bruno Mombrinie, Forestville, CA (US); Jeff Brian Eidsen, Windsor, CA (US); Cindy Carol Eidsen, Windsor, CA (US); Joe Peterson, Windsor, CA (US); Robert Davis, Santa Rosa, CA (US)

(73) Assignee: Haleys Pump Company, Forestville, CA (US)

( * ) Notice: Subject to any disclaimer, the term of this patent is extended or adjusted under 35 U.S.C. 154(b) by 628 days.

(21) Appl. No.: 11/163,758

(22) Filed: Oct. 28, 2005

(65) Prior Publication Data

US 2008/0275381 A1 Nov. 6, 2008

Related U.S. Application Data

(63) Continuation-in-part of application No. 10/419,325, filed on Apr. 18, 2003, now Pat. No. 7,294,120.

(60) Provisional application No. 60/623,290, filed on Oct. 28, 2004, provisional application No. 60/373,797, filed on Apr. 18, 2002.

(51) Int. Cl.
*A61M 5/14* (2006.01)
*A61M 37/00* (2006.01)
(52) U.S. Cl. ............... 604/257; 604/131; 604/4.01
(58) Field of Classification Search ....... 604/4.01–6.16, 604/31, 257, 259, 260, 264, 317, 540
See application file for complete search history.

(56) References Cited

U.S. PATENT DOCUMENTS

| 3,650,404 | A  | * | 3/1972  | Versaci ................... 210/238 |
| 4,222,377 | A  | * | 9/1980  | Burton .................... 600/31 |
| 4,766,889 | A  | * | 8/1988  | Trick et al. ............... 600/40 |
| 6,485,465 | B2 | * | 11/2002 | Moberg et al. ............ 604/154 |
| 2002/0115933 | A1 | * | 8/2002 | Duchon et al. ............ 600/432 |

* cited by examiner

*Primary Examiner*—Nicholas D Lucchesi
*Assistant Examiner*—Rebecca E Eisenberg
(74) *Attorney, Agent, or Firm*—Gary Hoenig

(57) ABSTRACT

The present invention relates to an improved apparatus and method for instilling fluid into a patient having an intestinal stoma thereby administering an antegrade colonic enema. The portable instillation apparatus comprising in combination: a fluid reservoir, a pump assembly, a control module, a fluid delivery line and an intestinal stoma catheter wherein the control module is operable to automatically stop fluid delivery to the intestinal stoma after a predetermined volume of fluid has been instilled at a predetermined flow rate and pressure range suitable for a particular patient. The portable instillation apparatus incorporates a unique gear pump manifold facilitating the portability, durability and reliability of the apparatus overcoming the disadvantages of traditional peristaltic pump mechanisms. The portable instillation apparatus is so engineered as to maximize the ease of transport and use of the device while also enabling a method for a patient to self-administer an antegrade colonic enema within a short time period and without intervention.

14 Claims, 4 Drawing Sheets

PORTABLE INSTILLATION APPARATUS AND METHOD

This patent application is a non-provisional application of U.S. Provisional Application Ser. No. 60/623,290 filed Oct. 28, 2004, for which priority is claimed and whose disclosure is hereby incorporated by reference in its entirety. Application Ser. No. 60/623,290 which, in turn, is a Continuation-In-Part of U.S. patent application Ser. No. 10/419,325 filed Apr. 18, 2003, now U.S. Pat. No. 7,194,120 for which priority is claimed and whose disclosure is hereby incorporated by reference in its entirety. Application Ser. No. 10/419,325 which, in turn, is a Continuation-In-Part of U.S. Provisional Application Ser. No. 60/373,797 filed Apr. 18, 2002, for which priority is claimed and whose disclosure is hereby incorporated by reference in its entirety.

BACKGROUND OF THE INVENTION

The present invention relates to a human large intestine flushing apparatus such as required for patients with large intestinal disorders including fecal incontinency or intractable constipation. More particularly, to an apparatus for automatic installation of flushing fluids to the large intestine for managing bowel movements in patients exhibiting fecal incontinency, intractable constipation or related disorders who have undergone a Malone type, Monti plasty or similar surgical procedure wherein a catheterizable stoma is constructed into the large intestine allowing insertion of the installation apparatus for the purpose of administering an Antegrade Colonic or Continent Enema (ACE).

Medical disorders of the large intestine can result in symptoms which prevent the patient from adequately evacuating fecal material from the large intestine. Fecally incontinent and intractably constipated patients have difficulties managing their bowel movement. Bowel movement management is typically accomplished by a daily flushing of the large intestine by enema wherein fluids are introduced into the large intestine to flush materials retained in the intestine. Fluids can be introduced from the rectum into the large intestine to flush and allowed to drain out. There are disadvantages with the application of a rectal enema flush including the lack of penetration of fluid throughout the entire interior of the large intestine, thereby leaving fecal matter lodged in the intestine, cleanliness issues, general difficulty of self application, lack of privacy, discomfort, and bulky enema equipment.

Surgical techniques have been developed to permit the application of an enema into the large intestine from the top of the intestine as opposed to the rectum. The enema from above or Antegrade Colonic Enema requires that a patient undergo a surgical procedure to create a stoma or entry through the skin into the intestine proximal to the top of the large intestine, principally to the cecum. Fluids are introduced and permitted to flush and drain to and out the rectum. Several surgical procedures have been developed to construct an entry point intestinal stoma proximal to the cecum. The Malone or Continent Appendicostomy surgical procedure constructs a connection conduit made between the appendix and the navel (belly-button) wherein a "button" or piercing is created at the navel. Using the "button" the patient can insert a needle or catheter and deliver fluid, a process known as instillation, into the large intestine as an alternative to performing a rectal enema. The procedure permits use of the appendix or neoappendix to be used as a way to administer an antegrade colonic enema or an antegrade continent enema without a rectal maneuver.

Another similar procedure known as a Monti plasty procedure surgically fashions a conduit between the large intestine and an insertion stoma in the skin also for purposes of instillation of an antegrade colonic enema.

Regardless of the technique elected to create a stoma entry into the large intestine, the installation of fluids requires an external mechanism to introduce the fluids into the stoma and therefore into the intestine. Fluid is typically introduced to sweep the large intestine of fecal matter at least once a day.

Prior to the present invention, patients who have undergone a Malone, Monti or similar surgical procedure have been required to introduce fluids into the large intestine by means of a drip consisting typically of a saline filled bag elevated above the patient with a drain tube attached at one end to the bag and terminated by a needle or catheter at the other end which, in turn, is inserted into the button or piercing at the navel. Fluid is permitted to drip into the large intestine which migrates to the rectum and the flushing is accomplished. The drip procedure requires the patient to remain immobile and sitting on a commode as the fluid passes through the intestine and out the rectum for a period of several hours. The procedure typically requires on standard drip bag to be used.

More recently, flushing of the intestine through the entry stoma piercing has been accomplished by introducing fluids into the large intestine by utilizing a series of fluid-filled syringes. A large syringe filled with the flushing fluid is attached to a needle or catheter and inserted into the piercing or button. The fluid contents of the syringe is dispensed and then refilled periodically until the required amount of fluid is delivered. The syringe technique requires two competent people to administer. One caretaker is required to fill the syringe. At the same time the patient is responsible for pinching the catheter shut when the syringe is removed from the catheter as introduction of flushing fluid into the intestine produces back pressure. The catheter must be pinched shut to prevent fecal matter and intestinal fluid from flowing back through the catheter and out the now open catheter end when the syringe is removed for filling. The procedure using the syringe technique requires the syringe to be refilled 10 to 20 times. If the client is not competent or able enough to assist, a second caretaker is needed. Many individuals requiring this type of treatment often have other handicaps that prevent them from assisting themselves. The use of multiple syringes also increases the risk of introducing air into the installation fluid. The introduction of air into the stoma necessarily induces significant discomfort or pain in the patient.

Automated instillation devices directed to address the disadvantages of the drip bag and syringe techniques exhibit the principle disadvantage associated with the difficulty to manipulate the various elements of the device as required during self-administration, usually requiring the use of both hands for manipulation. Devices with separate fluid reservoir bags must be separated from the apparatus in preparation to fill the reservoir bag a manuvour that requires dexterity not always present in patients requiring the apparatus. Further, separation of the fluid reservoir can introduce air into the pump potentially causing discomfort to the patient during the administering the procedure.

In order to determine when a predetermined volume of instillation flushing fluid has been delivered, a pump control system may monitor the pump motor current and stop the pump motor with the pump motor current draw increase as a sealed collapsible fluid reservoir is depleted of fluid. The disadvantage of this technique is that current draw from the pump varies between pumps, the viscosity of flushing fluid, and the varying fluid resistance resulting from using differing sizes of catheters, thereby resulting in difficulties starting the apparatus and causing the pump to run dry.

There is a need for an improved instillation apparatus and method to administer an antegrade colonic that avoids these disadvantages. The present invention fulfills this need, and further provides related advantages.

SUMMARY OF THE INVENTION

Accordingly, the present invention is directed to colonic instillation pumps and, more specifically, to such an apparatus with improved portability, reliability and user convenience.

The present invention further improves the portability and ease of use of prior art devices by uniquely integrating all pump components into a single unit. Prior art teachings utilize a number of components that are strung together and are difficult for many patients to manipulate sometimes requiring additional caregivers to assist. The present invention therefore generally comprises a fluid reservoir having a top and a bottom suitable for holding instillation fluid, an internal component chamber having a top and a bottom wherein the chamber top is formed from the fluid reservoir bottom, a pump manifold assembly mounted to the bottom of the fluid reservoir and inside the internal component chamber having an inlet and an outlet with the inlet in direct fluid communication with the fluid reservoir and the outlet protruding upwardly through the bulkhead into the fluid reservoir but not in fluid communication with the reservoir, a delivery tube being flexible and having a proximal and distal end with the proximal end in direct fluid communication with the pump manifold outlet, a catheter suitable for insertion into a patient with an intestinal stoma constructed for purposes of instilling fluid into a patient's intestines in direct fluid communication and removably attached to the distal end of the delivery tube, a pump control module communicatively attached to the pump manifold assembly for purposes of activation and mounted in the internal component chamber, a fluid level sensor mounted in the fluid reservoir operable to communicate the presence of fluid in the reservoir to the pump control module to which it is communicatively attached, the pump control module further being in direct electrical communication with a power supply, and a user interface module mounted proximate to the internal component chamber being in direct electrical communication with the pump control module.

The method of using the present invention to self-administer an antegrade colonic enema comprises the steps of; filling the reservoir with a flushing fluid, inserting the catheter suitable for insertion into a patient with an intestinal stoma, activating the apparatus, waiting for the apparatus to automatically deactivate, removing the catheter from the patient. The operation is therefore simple and within the capabilities of most patients, including those with disabilities.

Reduced manufacturing costs are accomplished by eliminating the need for molds to be produced as the pump body may be fabricated from stock sizes of polymer tubing.

As the pump is intended to be portable, in normal use the pump is periodically subjected to inspection such as at airports and other such security points, an objective of the invention is therefore to minimize the burden of security inspection procedures. Use of transparent materials for the construction of the housing of the pump enables convenient visual inspection of the pump's internal components thereby improving ease of transit with the pump. Further a flexible delivery tube, being connected within the bottom of the fluid reservoir permits easy storage of the tube within the fluid reservoir for transport.

Of noteworthy import, the present invention utilizes a unique integrated pump manifold assembly. Cleanliness of the fluid flow paths in devices that deliver fluid to the body is important. Keys to maintaining the cleanliness of the pathway include reducing the overall path length, minimizing back flow, and to reduce the number of crevices or surface imperfections where debris may collect. Peristaltic pumps, well know to those in the field, are typically used in the prior art because the peristaltic pumps do not require a back flow restriction device and the activating surfaces of the pump are comprised of a flexible tube, known as a tube set, which is squeezed. The tube set has a smooth interior and requires replacement. Unfortunately peristaltic pumps are large and bulky compared to gear pumps with similar volume capabilities. And, repeated squeezing of the tube set eventually results in sloughing of material from the tube into the delivered fluid as the tube wears. Consequently, the tube set must be replaced frequently. Peristaltic pumps also consume more power than gear pumps. The characteristics of peristaltic pumps are therefore not suitable for small and portable instillation pumps. The pump manifold assembly of the present invention overcomes these disadvantages by incorporating a gear pump in combination with a fluid flow direction restrictor that permits the use of a gear pump. The fluid flow direction restrictor is located in the fluid path of the manifold and prevents back flow into the delivery tube and the reservoir through the gear pump. Further the restrictor requires a small fluid pressure in order to allow a forward flow thereby assuring firm seating of a valve ball on the valve seat in the restrictor and hence a secure seal. Still further by integrating the fluid flow direction restrictor in-line and in close proximity to the gear pump, the fluid path can be constructed in such a fashion that it is short and having a smooth interior while gaining the advantages of the reliability of gear pumps.

Typical backflow restrictors utilize a diaphragm construction that tend to allow backflow at low pressures and also provide surface areas where deposits can collect. The smooth surface of the valve ball and small valve seat surface area mitigate the buildup problem and prolong the life of the mechanism. A smooth surfaced glass material is used form the valve ball in the present invention.

Water and flushing fluid intrusion into the interior of prior art pumps manifests undesirable corrosion and deterioration of internal components thereby reducing the mean time to failure of the pump. The construction of the present invention utilizing a sealed interior component chamber increases reliability and availability of the apparatus by attaining improved water resistance over prior devices. Hence, a further objective of the invention is to provide an instillation pump that is water resistant for protection of the internal components and for more convenient cleaning.

BRIEF DESCRIPTION OF THE DRAWINGS

The accompanying drawings, which are incorporated in and constitute a part of this specification illustrate embodiments of the invention and, together with the description, serve to explain the features, advantages, and principles of the invention.

In the drawings.

DETAILED DESCRIPTION OF THE PREFERRED EMBODIMENT

Figure 1:
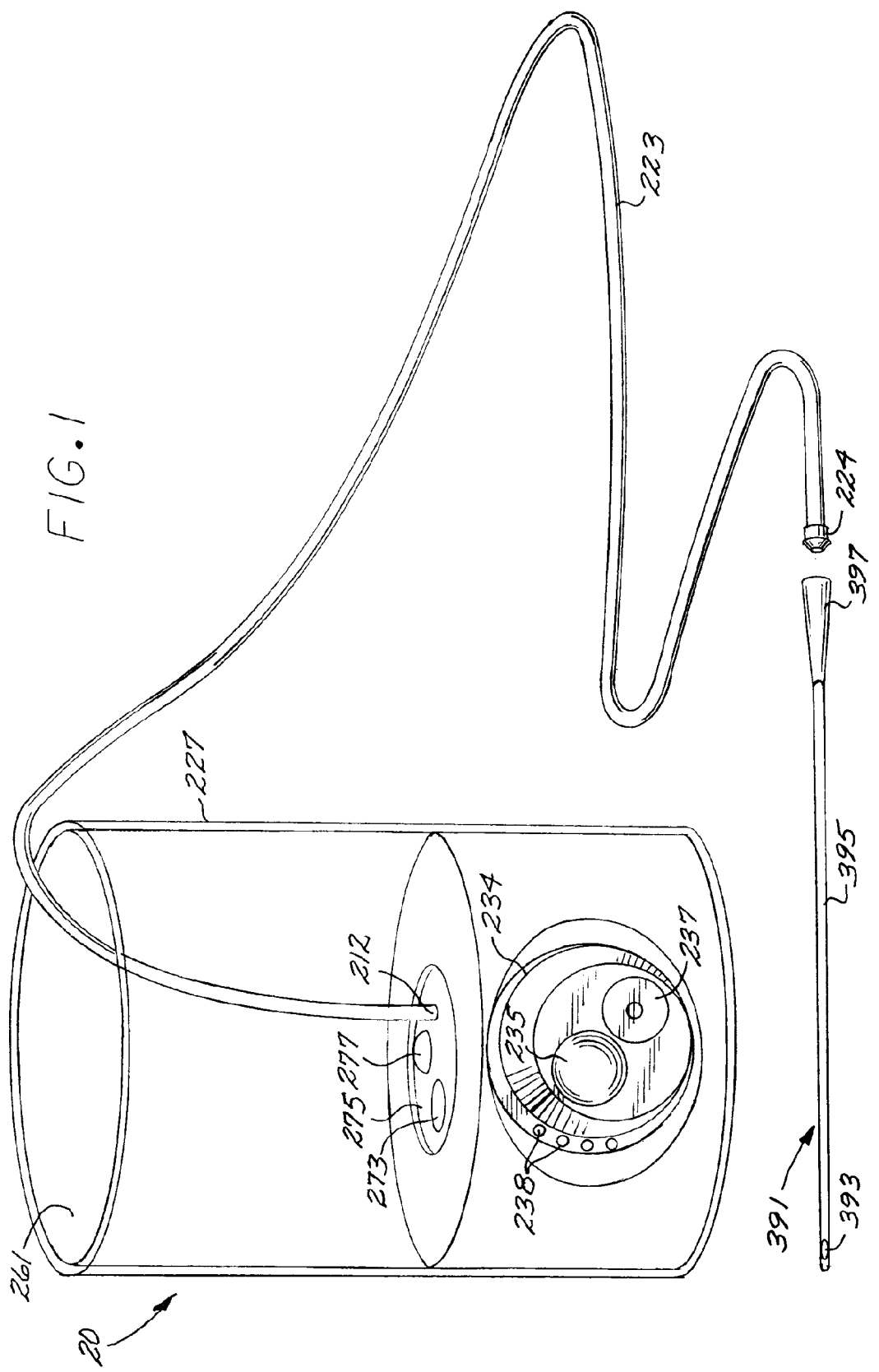
FIG. 1 is a perspective view of an embodiment of the portable instillation apparatus constructed in accordance with this invention when arranged so as to clearly illustrate the components of the pump assembly of the invention.

Although particular embodiments of the invention have been described in detail for purposes of illustration, various modifications may be made without departing from the spirit and scope of the invention. Accordingly, the invention is not to be limited except as by the appended claims. Referring now in greater detail to the various figures of the drawing wherein like reference characters refer to like parts, there is shown at 20 in FIG. 1, portable instillation apparatus constructed in accordance with the subject invention. Before describing the details of that apparatus it must be pointed out that while the apparatus is particularly suited for affecting an antegrade colonic enema, it can also be used of other similar irrigations of the intestines as well. Moreover, the subject invention can further be used for non-enema applications wherein instillation of a fluid is desired.

Figure 3:
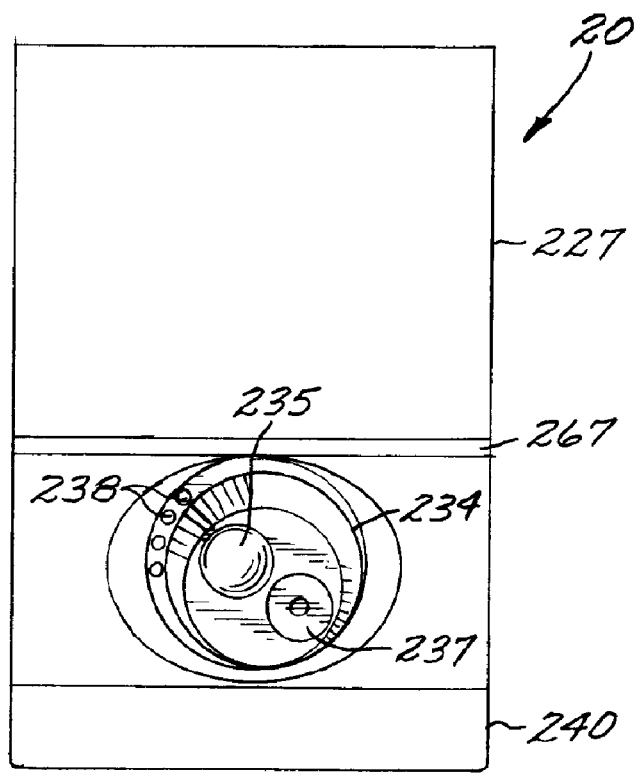
FIG. 3 is a front elevation view of the invention shown in FIG. 1.
Figure 4:
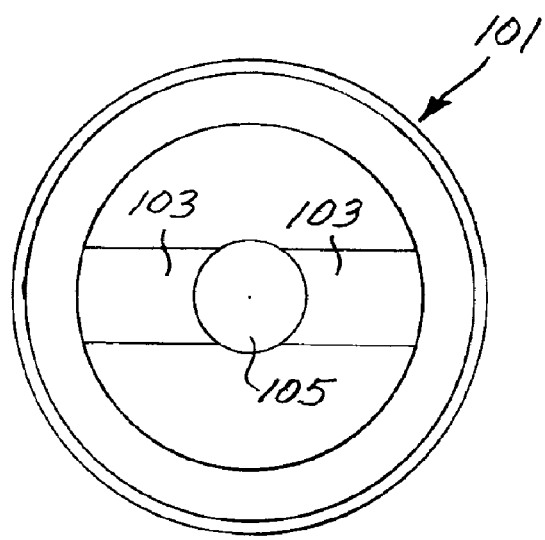
FIG. 4 is a top plan view of the invention shown in FIG. 1.
Figure 5:
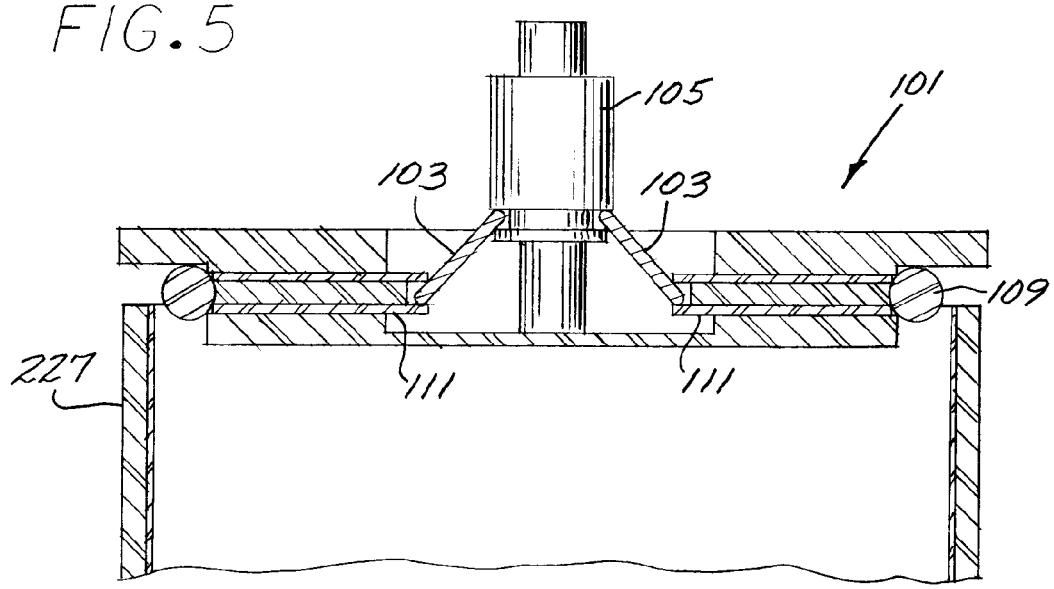
FIG. 5 is a sectional view of the lid assembly of the invention shown in the sealing position.
Figure 6:
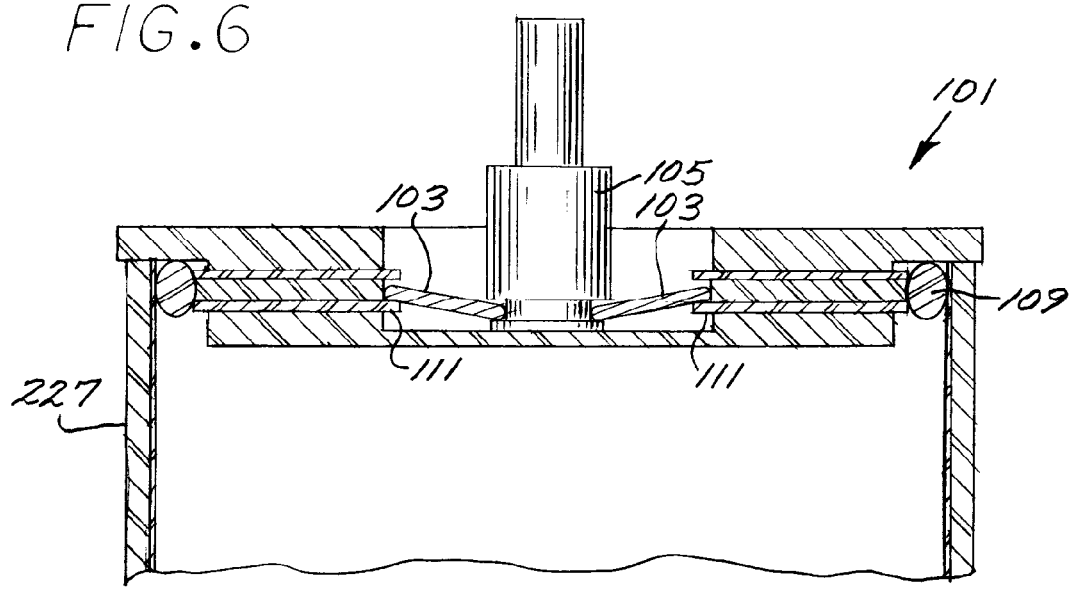
FIG. 6 is a sectional view of the lid assembly of the invention shown in the open position.

A preferred embodiment of the instant invention is illustrated in FIGS. 1-6. FIGS. 5-6 are directed to various arrangements the lid assembly of the invention to more particularly illustrate corresponding steps in the method of use of the invention.

In the embodiment, the present invention comprises a cylindrically shaped fluid reservoir having a top and a bottom, a circular bulkhead plate having a top and a bottom forming the bottom of the fluid holding portion of the reservoir and the top of a component chamber pressed and sealed into the inside circumference of cylinder of the fluid reservoir, the component chamber having a top and a bottom with bottom being a circular element inserted the inside circumference of the bottom of the cylinder of the fluid reservoir, thereby enclosing and protecting the chamber from fluid intrusion, the circular element further comprising a cavity accessible from the bottom of the element suitable for retaining a battery, a pump manifold mounted to the bottom of the bulkhead having an inlet and an outlet with the inlet in direct fluid communication with the fluid reservoir and the outlet protruding upwardly through the bulkhead into the fluid reservoir but not in fluid communication with the reservoir, the pump manifold further comprises a gear pump having a pump motor, the gear pump being in direct fluid communication with the manifold inlet and a flow direction restrictor, the restrictor being operable to permit flow in a direction from the manifold inlet, the restrictor being in further, direct fluid communication with the manifold outlet, a delivery tube being flexible and having a proximal and distal end with the proximal end in direct fluid communication with the pump manifold outlet, a catheter suitable for insertion into a patient with an intestinal stoma constructed for purposes of instilling fluid into a patient's intestines in direct fluid communication and removably attached to the distal end of the delivery tube, a pump control module communicatively attached to said gear pump motor suitable for activating the pump motor, an optical fluid level sensor mounted in the bulkhead operable to communicate the presence of fluid in the reservoir to the pump control module to which it is communicatively attached, the pump control module further being in direct electrical communication with the battery, a user interface module mounted to the cylinder proximate to the component chamber being in direct electrical communication with the pump control module, and a lid assembly being generally circular is detachably inserted into the circumference of the top of the fluid reservoir.

FIG 1 is an overall perspective view of the apparatus 20, showing the major subsystems and their spatial relationship. Referring to FIG. 1, the preferred embodiment of the portable instillation apparatus 20 comprises a cylindrically shaped fluid reservoir 227, a pump manifold assembly 249 (see FIG. 2) attached to the reservoir 227, a user control interface module 234 mounted in a vertical side of the reservoir electrically connected to the pump control module 263 (see FIG. 2) wherein the user controlled activation module comprises the user interface control button 237, indicators 238, and external power supply connections; and, a rechargeable battery and pump control module circuitry capable of driving the pump manifold assembly 249 (see FIG. 2). Alternate reservoir shapes may be used; however, a cylindrically shaped reservoir has been found to minimize manufacturing costs, an objective of the invention. Fluid delivery tube 223 is removably attached to the pump manifold assembly outlet 212. The distal end 224 of the fluid delivery tube 223 is removably attached to a catheter assembly 395 at 397. The tip 393 of catheter 391 is suitable for insertion into a patient's intestinal stoma. Of notable significance is the present invention provides overcomes a disadvantage of the prior art reducing the number of items requiring user attention. Flushing fluid is delivered to the reservoir by the patent. The patent inserts the catheter into their intestinal stoma. The apparatus is activated by pressing the start/stop operator control button 237 on the user interface module 234 activating the pump control module 263 (see FIG. 2) to which the button is electrically connected at 247. The pump is activated by a single assertion of the control button 237 by the operator. The pump control module activates the pump in the pump manifold 249 to deliver flushing fluid until the fluid reservoir is empty as detected by the optical fluid level sensor 277 when the pump control module automatically stops the pumping action and returns to rest mode.

Figure 2:
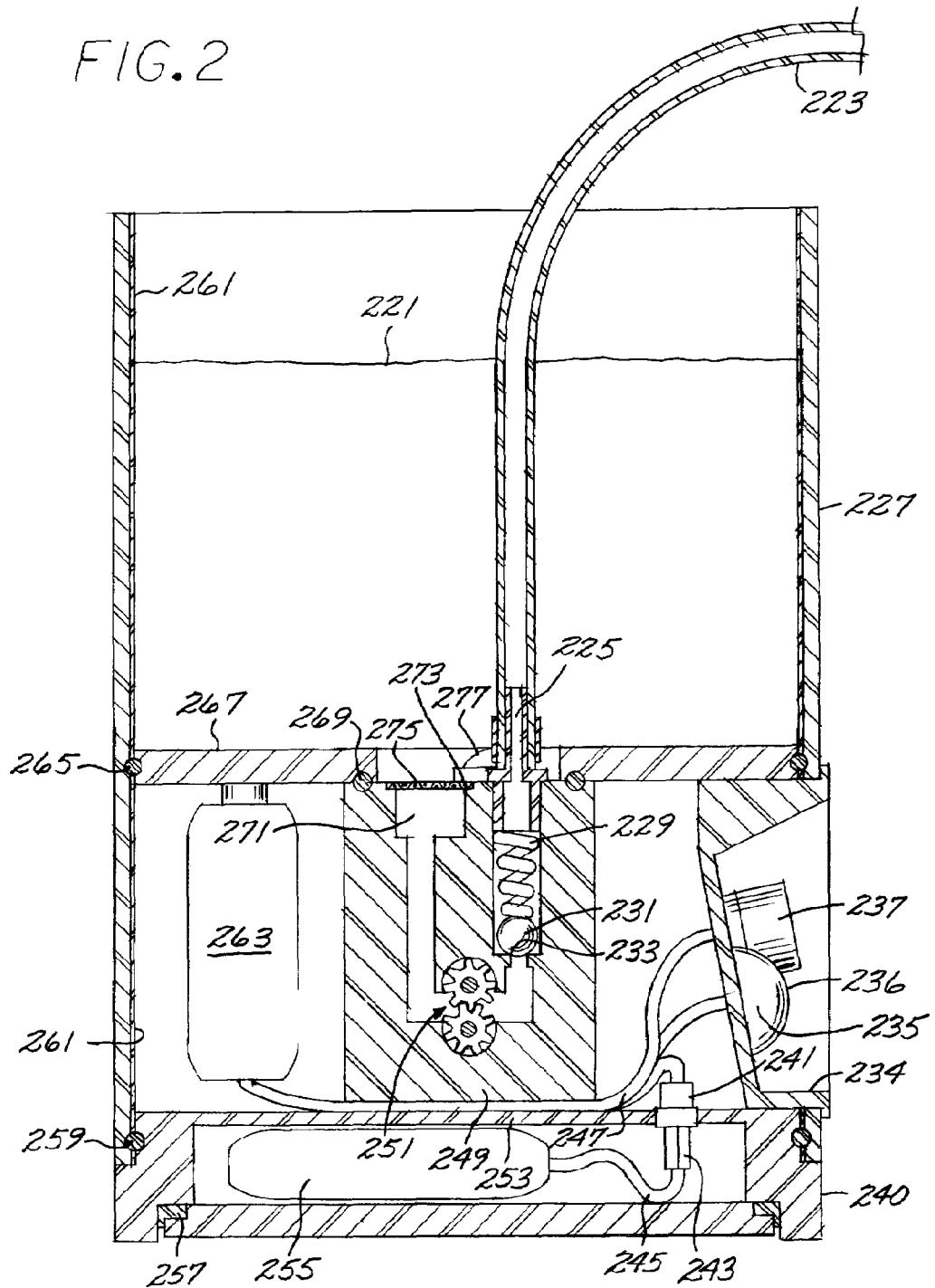
FIG. 2 is a left-side elevation sectional view of an embodiment of the pump assembly of the invention shown in FIG. 1.

Referring to FIG. 2, the fluid pumping action of the apparatus is accomplished through an inlet fluid strainer 273 inserted and pressed into a fluid inlet port 271 connectively attached to an integral gear pump head 251, further connectively attached to a one way fluid flow direction restrictor comprising valve ball seat 233, pressure valve ball 231 and pressure valve spring 229, also connectively attached to a fluid outlet port 225 comprising a press fit connector to receive one end of a flexible delivery tube 223. Both the fluid inlet 271 and outlet ports 225 are positioned in the bottom of a fluid reservoir 227 created by placement of bulkhead 267. The fluid flow direction restrictor prevents back flow of fecal matter back up through the catheter into the apparatus. The bulkhead 267 the fluid inlet 271 and optical fluid level sensor 277 are positioned in a recess 275 in the bulkhead 267 so as to not to prematurely deactivate the pump control module 263 as the fluid level 221 in the reservoir decreases. The internal component chamber is created by the bulkhead 267 inserted with seals 265 and 269 in the fluid reservoir and an end element 240 inserted into the bottom of the reservoir cylinder with seal 259 thereby forming a water-tight enclosure for the pump control module, the pump manifold and user interface control. If the reservoir cylinder is constructed of a transparent material, optically low impedance reflective surface element 261 can be optionally installed for decorative purposes while permitting limited visual inspection of the interior components. The end element 240 has a recessed cavity enclosed by bottom plate 253 with seal 257 wherein a rechargeable battery 255 with cable 245 is inserted. Feed through connectors 241 and 243 provide water-tight electrical connectivity between the battery 255 and the pump control module 263. Feed through connector 243 is reserved for connecting an external battery directly to the pump motor in the pump manifold so as to allow operation of the apparatus in the event that the pump control module fails.

The sectional view of user control interface module 234 is also illustrated in FIG. 2. More clearly illustrated in FIG. 1, the user control interface comprises a single push button control 237 provides simple user start/stop control. When finished using the apparatus, the patent simply stows the delivery tube 223 and catheter assembly 395 in the fluid reservoir and replaces the lid assembly. The patient may stop the apparatus while active and before the apparatus has automatically stopped by pressing the user stop/start control again. Electrical connector 235 with watertight cover 236 (see FIG. 2) accepts connection from an external charging unit. Indicators 238 provide various information to the user including battery condition, charging status, and operating mode.

FIG. 3 shows the user control interface module 234 as observed by the patient from the exterior of the pump assembly in a front elevation view of the apparatus.

Referring to FIG. 4, a top plan view of the embodiment so arranged in the transport configuration, wherein the lid assembly is inserted into the open top of the cylindrical fluid reservoir 227.

FIG. 5 shows the lid assembly of the embodiment of the invention in the open position. The lid assembly provides a water-tight seal with 0-ring 109 against the interior circumference of the cylindrically shaped fluid reservoir 227. The 0-ring 109 is expanded and contracted in circumference length by wedges 111 constrained by lid cover 101 so as to slide inwardly and outwardly along the radius of the lid cover. Detent springs 103 are hingedly attached to both the wedges 111 and knob 105. Knob 105 slides vertically along the central shaft of the lid cover 101. When the knob is slid downwardly, detent springs 103 force wedges 111 outwardly along the radius of the lid cover there by expanding the total circumference of the lid and hence the o-ring 109, thus compressing the o-ring 109 against the interior circumference of the reservoir 227.

FIG. 6 shows the lid assembly of FIG. 5 in the closed position wherein the o-ring 109 is compressed against the interior circumference of the reservoir 227.

Use of the portable instillation apparatus is very simple and can be managed by a patient or caregiver with very little training. As many patients use tap water as the flushing fluid for antegrade colonic enemas, the open reservoir system provides easy filling direction from a sink faucet as well as easy access for cleaning.

Moreover, the new system provides facile utilization due to: (1) minimal patient training, (2) no filling of reservoir bags or other sealed containers, (3) an open, bottom drawn reservoir system providing easy filling with minimal air entrainment, and (4) ready portability.

In view of the foregoing, it will be seen that the several objects of the invention are achieved and other advantages are attained. Although the foregoing includes a description of the best mode contemplated for carrying out the invention, various modifications are conceivable.

What is claimed is:

1. A portable instillation apparatus for the purpose of pumping fluid into the intestinal tract through a stoma opening as presented by a patient, comprising, a fluid reservoir having a top and a bottom suitable for holding instillation fluid, the bottom being a bulkhead, a component chamber positioned below the fluid reservoir having a top and a bottom wherein the chamber top is formed from the fluid reservoir bulkhead, a pump manifold assembly mounted to the fluid reservoir bulkhead and inside the component chamber having an inlet and an outlet with the inlet in direct fluid communication with the fluid reservoir and the outlet protruding upwardly through the bulkhead into the fluid reservoir but not in fluid communication with the reservoir, a delivery tube being flexible and having a proximal and distal end with the proximal end in direct fluid communication with the pump manifold outlet, a catheter suitable for insertion into a patient with an intestinal stoma constructed for purposes of instilling fluid into a patient's intestines in direct fluid communication and removably attached to the distal end of the delivery tube, a pump control module communicatively attached to the pump manifold assembly for purposes of activation and mounted in the component chamber, a fluid level sensor mounted in the fluid reservoir operable to communicate the presence of fluid in the reservoir to the pump control module to which it is communicatively attached, the pump control module further being in direct electrical communication with a power supply; and, a user control interface module mounted proximate to the component chamber being in direct electrical communication with the pump control module.

2. The portable instillation apparatus of claim 1 wherein the pump manifold assembly further comprising further a gear pump having a pump motor, the gear pump being in direct fluid communication with the manifold assembly inlet and a fluid flow direction restrictor, the restrictor being operable to permit flow in a direction from the manifold inlet, the restrictor being in further, direct fluid communication with the manifold assembly outlet.

3. The portable instillation apparatus of claim 2 wherein the fluid flow direction restrictor comprises a load spring applying a preselected force between the body of the pump manifold assembly and a valve ball along the fluid communication pathway in the direction of the pump manifold assembly inlet, and a valve seat in the fluid communication pathway fixed to the pump manifold assembly thereby forming a seal between the valve ball and valve seat restricting the fluid flow in a direction from the inlet to outlet to flows exhibiting pressures sufficient to over come the preselected force of the load spring and stopping the fluid flow in a direction from the outlet to the inlet.

4. The portable instillation apparatus of claim 1 further comprising a lid assembly detachably inserted into the top of the fluid reservoir.

5. The portable instillation apparatus of claim 4 wherein the lid assembly further comprises a cover having a circumference length and radius, and an o-ring capable of being expanded and contracted in the circumference length by wedges constrained by the cover so as to slide inwardly and outwardly along the radius of the cover.

6. The portable instillation apparatus of claim 1 wherein the fluid reservoir is cylindrically shaped.

7. The portable instillation apparatus of claim 1 wherein the user interface module further comprises at least one operator control button in electrical connectivity with the pump control module for activating and deactivating the pump control module such that the pump control module is activated by a single assertion by the operator.

8. The portable instillation apparatus of claim 1 wherein the fluid level sensor is an optical fluid level sensor.

9. The portable instillation apparatus of claim 1 wherein the component chamber is constructed of transparent materials so as to permit viewing of the components inside the component chamber.

10. The portable instillation apparatus of claim 1 wherein the component chamber is constructed of optically low impedance reflective materials with sufficient transparency so as to permit viewing of the components inside the component chamber.

11. The portable instillation apparatus of claim 1 wherein the power supply is rechargeable batteries.

12. The portable instillation apparatus of claim 1 wherein the power supply is an external battery supply.

13. A method of using the portable instillation apparatus of claim 1 comprising the steps of, filling the reservoir with a flushing fluid, inserting the catheter suitable for insertion into a patient with an intestinal stoma, activating the apparatus, waiting for the apparatus to automatically deactivate, and removing the catheter from the patient.

14. A portable instillation apparatus for the purpose of pumping fluid into the intestinal tract through a stoma opening as presented by a patient, comprising,

- a cylindrically shaped fluid reservoir having a top, a bottom and a fluid holding portion,
- a circular bulkhead plate having a top and a bottom forming the bottom of the fluid holding portion of the reservoir and the top of an internal component chamber pressed and sealed into the inside circumference of cylinder of the fluid reservoir, the internal component chamber having a top and a bottom with bottom being a circular element inserted the inside circumference of the bottom of the cylinder of the fluid reservoir, thereby enclosing and protecting the chamber from fluid intrusion, the circular element further comprising a cavity accessible from the bottom of the element suitable for retaining a battery,
- a pump manifold assembly mounted to the bottom of the bulkhead having an inlet and an outlet with the inlet in direct fluid communication with the fluid reservoir and the outlet protruding upwardly through the bulkhead into the fluid reservoir but not in fluid communication with the reservoir, the pump manifold assembly further comprises a gear pump having a pump motor, the gear pump being in direct fluid communication with the manifold inlet and a fluid flow direction restrictor, the restrictor being operable to permit flow in a direction from the manifold assembly inlet, the restrictor being in further, direct fluid communication with the manifold assembly outlet,
- a delivery tube being flexible and having a proximal and distal end with the proximal end in direct fluid communication with the pump manifold outlet,
- a catheter suitable for insertion into a patient with an intestinal stoma constructed for purposes of instilling fluid into a patient's intestines in direct fluid communication and removably attached to the distal end of the delivery tube,
- a pump control module communicatively attached to said gear pump motor suitable for activating the pump motor,
- an optical fluid level sensor mounted in the bulkhead operable to communicate the presence of fluid in the reservoir to the pump control module to which it is communicatively attached, the pump control module further being in direct electrical communication with the battery,
- a user interface module mounted to the cylinder proximate to the component chamber being in direct electrical communication with the pump control module; and,
- a lid assembly being generally circular is detachably inserted into the circumference of the top of the fluid reservoir.

* * * * *